United States Patent [19]

Darsow et al.

[11] Patent Number: 5,786,521
[45] Date of Patent: Jul. 28, 1998

[54] PROCESS FOR PREPARING HYDROXYMETHYLCYCLOPROPANE

[75] Inventors: Gerhard Darsow, Krefeld; Lutz Frohn, Erkrath; Reinhard Langer, Krefeld, all of Germany

[73] Assignee: Bayer Aktiengesellschaft, Leverkusen, Germany

[21] Appl. No.: 818,588

[22] Filed: Mar. 14, 1997

[30] Foreign Application Priority Data

Mar. 21, 1996 [DE] Germany .................. 196 11 142.0

[51] Int. Cl.⁶ .................................................. C07C 27/10
[52] U.S. Cl. ................................................................. 568/700
[58] Field of Search ........................... 568/814, 822, 568/700; 560/8, 129; 502/340, 343, 346

[56] References Cited

U.S. PATENT DOCUMENTS 4,720,597  1/1988  Otte et al. .
5,008,235  4/1991  Wegman et al. .

Primary Examiner—Gary Geist
Assistant Examiner—Karl J. Puttlitz, Jr.
Attorney, Agent, or Firm—Sprung Kramer Schaefer & Briscoe

[57] ABSTRACT

Hydroxymethylcyclopropane is prepared from alkyl cyclopropanecarboxylates by reduction with hydrogen in a process in which use is made of a reduced pelletized catalyst which is obtainable by pressing a mixture of pulverulent copper, zinc and aluminum oxides and subsequent reduction. This process has the advantage that it uses a low-toxicity catalyst which has a long operating life and is particularly suitable for a continuous process and requires relatively low reaction temperatures.

9 Claims, No Drawings

PROCESS FOR PREPARING HYDROXYMETHYLCYCLOPROPANE

The present invention relates to a process for preparing hydroxymethylcyclopropane by catalytic hydrogenation of alkyl esters of cyclopropanecarboxylic acid with hydrogen using a fixed-bed catalyst.

Hydroxymethyl-cyclopropane is used for the preparation of pharmaceutical products and crop protection agents.

It is known that hydroxymethyl-cyclopropane can be prepared by catalytic hydrogenation of cyclopropanecarboxylic esters (see U.S. Pat. No. 4,720,597). This process is carried out using a zinc-chromium catalyst which is particularly toxic because of its chromium content, has only a short life and requires reaction temperatures of above 200° C., for example from 250° to 300° C.

It is therefore desirable to have a catalyst for preparing hydroxymethylcyclopropane by hydrogenation of cyclopropanecarboxylic esters which is less toxic, has an increased life and can be employed at lower reaction temperatures.

It has now been found that the requirements mentioned are met by a reduced pelletized catalyst which is obtainable by pressing a mixture of pulverulent copper, zinc and aluminum oxides and subsequent reduction. Preferably, the pulverulent oxide mixture additionally contains at least one oxide of a metal of the iron group of the Periodic Table of the Elements (Mendeleev).

A process has thus been found for preparing hydroxymethyl-cyclopropane from alkyl cyclopropanecarboxylates, which comprises hydrogenating alkyl Cyclopropanecarboxylates with excess hydrogen at reaction temperatures of from 100° to 190° C. and a hydrogen pressure of from 30 to 400 bar in the presence of a reduced, pelletized catalyst which is obtainable by pressing a mixture of pulverulent copper, zinc and aluminum oxides and subsequent reduction.

Alkyl cyclopropanecarboxylates which are suitable for use in the process of the invention are, for example, ones in which the alkyl radical has from 1 to 10 carbon atoms. Examples of such alkyl radicals are methyl, ethyl, propyl, butyl, isobutyl, pentyl, hexyl, octyl and decyl. Preference is given to methyl, ethyl, propyl, butyl, isobutyl and hexyl. Particular preference is given to methyl, ethyl, propyl, butyl and isobutyl.

According to the invention, the hydrogenation is carried out using an excess of hydrogen. The amount of hydrogen can be, for example, from 10 to 60 times the stoichiometrically required amount.

The pressure range for the process of the invention is in the range from 30 to 400 bar. Preference is given to from 120 to 350 bar, particularly preferably from 250 to 320 bar.

According to the invention, the hydrogenation is carried out at a temperature of from 100° to 190° C. The temperature is preferably in the range from 130° to 180° C.

It is possible to carry out the process of the invention with addition of a solvent or solvent mixture. Suitable solvents are those customary for catalytic hydrogenations, e.g. aliphatic alcohols. However, since the presence of solvents makes the distillative work-up of the reaction mixture more difficult, preference is given to carrying out the process without addition of solvents.

The process of the invention can be carried out, for example, in the gas or liquid phase. Carrying it out in the liquid phase, e.g. in a trickling phase, is preferred.

The hydrogenation of esters is frequently carried out using batchwise processes in which pulverulent catalysts are employed in suspended form. In contrast thereto, the process of the invention can be carried out continuously using a pelletized catalyst and with a long operating life of the catalyst. This avoids the handling problems which are unavoidable in the case of pulverulent catalysts, e.g. the difficulty of activating pulverulent catalysts uniformly and in a targeted manner, the difficulty of circulating them by means of slurry pumps and the difficulty of separating them completely from the reaction product. Slurry pumps are very prone to wear because they are subject to high mechanical stresses. The complete removal of pulverulent catalysts is complicated because it requires a coarse filtration and a fine filtration and the filters for alternating operation and purification have to be present at least in duplicate in each case. In addition, there is a great danger of pulverulent catalysts quickly losing their activity as a consequence of the circulation and filtration, which results in high catalyst consumptions and short catalyst operating lives. In contrast to these difficulties, pelletized catalysts to be used according to the invention are more easily handled and have a high activity which is retained over periods of, for example, up to several years. The latter advantage is particularly important since such long catalyst operating lives mean that replacement of the catalyst, which is costly even in the case of fixed-bed catalysts, is needed only rarely.

The pelletized catalyst to be used according to the invention is obtainable from a mixture of pulverulent copper, zinc and aluminum oxides. In the pulverulent oxide mixture, the proportion of copper can be, for example, from 40 to 60% by weight, the proportion of zinc can be, for example, from 15 to 30% by weight and the proportion of aluminum can be, for example, from 0.2 to 6% by weight, with these figures being based on the total amount of the pulverulent oxide mixture and the remainder to 100% by weight being oxygen. The pulverulent oxide mixture can contain the oxides, for example, in a mean particle size of less than 200 µm. Among the copper oxides, preference is given to copper(II) oxide. A catalyst produced from such mixtures by pressing and reduction can be used without further additives in the hydrogenation according to the invention.

However, the pulverulent mixture advantageously additionally contains at least one oxide of a metal of the iron group of the Periodic Table of the Elements (Mendeleev). Preferred oxides for this purpose are oxides of iron, cobalt and/or nickel in which the metals can have the oxidation states +2 and/or +3. Particular preference is here given to iron(III) oxide. Oxides of iron, cobalt and nickel, preferably of iron and cobalt, can be used either individually or in admixture with other oxides of the metals mentioned. The total amount of oxides of metals of the iron group in the pulverulent oxide mixture can be, for example, from 0.1 to 1.5% by weight of the total oxide powder. Preference is given to from 0.05 to 1.0% by weight, in particular from 0.1 to 0.5% by weight. If a plurality of oxides of metals of the iron group are used, each one of these oxides can be present, for example, in an amount which is not less than 20% by weight and not more than 80% by weight of the total amount of oxides of metals of the iron group.

For the process of the invention, it is advantageous to use catalysts which are as free as possible of alkali metal and alkaline earth metal compounds. In any case, such impurities should be present in an amount of less than 0.1% by weight, based on the total amount of the pulverulent oxide mixture.

The production of a pelletized catalyst from the mixture of pulverulent oxides can be carried out by pressing using methods customary per se, for example under high pressure on tableting or pelletizing machines. If desired, graphite and/or adhesives, for example in amounts of up to 3% by weight based on the total weight of the constituents to be pressed, can be added to improve the adhesion of the metal oxide particles. The pressed catalysts can, for example, be in the form of tablets, spheres or granules having dimensions in the range from 2 to 10 mm, preferably from 3 to 7 mm. The pelletized catalyst bodies, in particular in the form of tablets, can be provided with a hole to increase the external surface area. Viewed macroscopically, such bodies have a smooth surface.

The pelletized catalysts are pressed in such a way that they have a compressive strength of, for example, from 50 to 200N, preferably from 75 to 150N, on the surface of the shaped body. In addition, the pelletized catalysts have an internal surface area of, for example, from 10 to 90 $m^2/g$, preferably from 30 to 80 $m^2/g$. The compressive strength of the pelletized catalysts can be determined, for example, in accordance with DIN 50 106, and the internal surface area can be determined, for example, by the method described in Analyt. Chem. 30, 1387–1392 (1958) or by the method of S.J. Gregg and S.W. Sing, Adsorption, Surface Area and Porosity, London 1982, chapters 2 and 6.

The shaped bodies to be used according to the invention as hydrogenation catalysts and comprising pressed powders of copper, zinc, aluminum and possibly further oxides have to be reduced before use. This is most simply carried out by treatment with hydrogen, for example at from 180° to 280° C. It is advantageous to use a mixture of, for example, from 10 to 15% by volume of hydrogen and from 90 to 85% by volume of inert gas (e.g. nitrogen) at the beginning of the treatment and to reduce the proportion of inert gas to zero during the course of the treatment. Such a treatment can, for example, be carried out over a period of from 10 to 35 hours. The treatment can be stopped when no more hydrogen is taken up and as a result no more water of reaction is formed.

In the hydrogenation reactor, the ester to be hydrogenated can flow from the bottom upward or from the top downward. It is advantageous to allow the ester to flow in gaseous or liquid form over the catalyst from the top downward (trickling phase). Here, the ester to be hydrogenated can flow over the catalyst either together with the separately introduced or previously mixed-in hydrogen (=cocurrent process) or can be conveyed in the opposite direction to the hydrogen (=countercurrent process).

The hydrogenation reactor can be, for example, a high-pressure tube of steel which is filled completely or partially with pelletized catalyst; in the case of relatively large tube cross sections, the use of the pelletized catalysts on trays (wire baskets or the like) is also a possibility. It is also possible to employ, for example, high-pressure tube bundles within a common jacket, with the individual tubes again being completely or partially filled with the pelletized catalysts.

In the process of the invention, the weight hourly space velocity over the catalyst can be, for example, from 200 to 600 g of ester per liter of catalyst. Under the other reaction conditions mentioned, long operating lives of, for example, from 8000 to 16,000 hours can be achieved with the catalysts to be used according to the invention, which makes them particularly suitable for continuous processes. For the catalysts described in U.S. Pat. No. 4,720,597, the operating life is generally only from 3000 to 4000 hours.

The reaction mixture leaving the hydrogenation reactor contains, after depressurization in which the excess hydrogen can be collected and after compression and replacement of the hydrogen consumed be used again, mainly hydroxymethylcyclopropane and the alcohol which corresponds to the alcohol part of the alkyl cyclopropanecarboxylate used. These two components can be separated by distillation. The hydroxymethyl-cyclopropane produced can, after being separated off by distillation, be obtained in a purity of up to 99.9% by weight. Product of this quality is directly suitable for further reactions.

Examples

Example 1

An upright, heat-insulated high-pressure tube of stainless, acid-resistant steel having an internal diameter of 45 mm and a length of 1 m, which had previously been flushed oxygen-free using nitrogen, was charged with 1.4 l of a hydrogenation catalyst produced by tableting powders of copper(II), zinc, aluminum and iron(III) oxides having a mean particle size of less than 200 µm. The copper content of the pellets was 42% by, weight, the zinc content was 17% by weight, the aluminum content was 2.0% by weight and the iron content was 0.2% by weight. The pellets had a height of 5 mm and a diameter of 5 mm, a compressive strength of 125N on the cylindrical surface and an internal surface area of 68 $m^2/g$.

For the activation by reduction, the pellets were first dried for 6 hours in a stream of nitrogen (temperature: max. 200° C.; flow rate: 5 standard $m^3/h$). The actual activation was carried out at a nitrogen pressure of 200 bar and a temperature between 180° and 280° C., with hydrogen being gradually being mixed into the inert gas in an amount which did not exceed 15% by volume in the initial phase. Over a period of 24 hours, the proportion of nitrogen in the gas mixture was reduced more and more until finally pure hydrogen flowed through the reactor. The activation was complete when no more water of reaction was formed, which was monitored using a downstream separator.

After activation of the hydrogenation catalyst, the hydrogen pressure in the reactor system was increased to 300 bar. Subsequently, 280 g/h of methyl cyclopropanecarboxylate together with 2 standard $m_3/h$ of hydrogen under a pressure of 300 bar were pumped through the high-pressure tube, with the methyl cyclopropanecarboxylate being heated in an upstream electrically heated heat exchanger to a temperature of 160° C. prior to entering the high-pressure tube.

The reaction product leaving the reaction tube was cooled to a temperature of below 60° C. in a second heat exchanger (water cooler) under 300 bar of hydrogen pressure and in a gas separator separated from the excess hydrogen which was returned to the hydrogenation system. After further cooling to a temperature below 30° C. and depressurization to atmospheric pressure, the reaction product was analyzed by gas chromatography.

The conversion of methyl cyclopropanecarboxylate was 99%, the selectivity to hydroxymethyl-cyclopropane was 98%. The catalyst was still highly active after a running time of 7600 hours.

Example 2

The procedure of Example 1 was repeated, but using a catalyst containing only 0.1% by weight of iron. The pellets had the same dimensions, compressive strengths and internal surface areas as described in Example 1. In this case, 320 g/h of ethyl cyclopropanecarboxylate were used in place of 280 g/h of methyl cyclopropanecarboxylate. According to analysis by gas chromatography, the conversion of ethyl cyclopropanecarboxylate was over 99.5% and the selectivity for the formation of hydroxymethylcyclopropane was 96%.

The catalyst had not yet lost any of its activity after a running time of 5800 hours.

Example 3

A high-pressure reactor as in Example 1 was charged under inert gas with 1.4 l of a hydrogenation catalyst produced by tableting powders of copper(II), zinc and aluminum oxide having a mean particle size of less than 200μm. The copper content of the pellets was 51% by weight, the zinc content was 19% by weight and the aluminum content was 0.5% by weight. The pellets had a height of 3 mm and a diameter of 3 mm, a compressive strength of 81N on the cylindrical surface and an internal surface area of 58 $m^2/g$.

After activation of the pellets by reduction as in Example 1, the hydrogen pressure was increased to 300 bar. Subsequently, 280 g/h of isobutyl cyclopropanecarboxylate together with 1.5 standard $m^3/h$ of hydrogen under a pressure of 300 bar were pumped continuously through the high-pressure tube, with the isobutyl cyclopropanecarboxylate being heated to a temperature of 160° C. prior to entering the high-pressure tube.

The reaction product leaving the reaction tube was worked up as described in Example 1 and analyzed by gas chromatography.

The conversion of isobutyl cyclopropanecarboxylate was 99.5%, the selectivity for the formation of hydroxymethylcyclopropane was 98%. The catalyst was still highly active after a running time of 6200 hours.

What is claimed is:

1. A liquid- or trickling-phase process for preparing hydroxymethylcyclopropane from alkyl cyclopropanecarboxylates, which comprises hydrogenating alkyl cyclopropanecarboxylates with excess hydrogen at reaction temperatures of from 100° to 190° C. and a hydrogen pressure of from 30 to 400 bar in the presence of a reduced pelletized catalyst having dimensions in the range from 2 to 10 mm, a compressive strength of from 50 to 200N on the surface of the shaped body, an internal surface area of from 10 to 90 $m^2/g$. and which is obtainable by pressing a mixture of pulverulent copper, zinc and aluminum oxides, said pulverulent mixture of oxides having a proportion of aluminum of from 0.2 to 6% by weight, and subsequent reduction.

2. The process as claimed in claim 1, wherein the alkyl radical in the alkyl cyclopropanecarboxylate used has from 1 to 10 carbon atoms.

3. The process as claimed in claim 1, wherein the amount of hydrogen used is from 10 to 60 times the stoichiometrically required amount.

4. The process as claimed in claim 1, carried out at from 150 to 350 bar and at from 130 to 180° C.

5. The process as claimed in claim 1, wherein the mixture of pulverulent copper, zinc and aluminum oxides additionally contains at least one oxide of a metal of the iron group of the Periodic Table of the Elements.

6. The process as claimed in claim 1, wherein the mixture of pulverulent oxides contains a proportion of copper of from 40 to 60% by weight, a proportion of zinc of from 15 to 30% by weight, a proportion of aluminum of from 0.2 to 6% by weight.

7. The process of claim 6, wherein the pulverulent oxides contain oxides of metals of the iron group up to a proportion of 1.5% by weight.

8. The process as claimed in claim 1, wherein the catalyst is reduced before use by treatment with hydrogen at from 180° to 280° C., using a mixture of from 10 to 15% by volume of hydrogen and from 90 to 85% by volume of inert gas at the beginning of the treatment and reducing the proportion of inert gas to 0 during the course of the treatment.

9. The process as claimed in claim 1, wherein the reaction mixture leaving the reactor is depressurized, excess hydrogen is collected and used again and the hydroxymethylcyclopropane formed and the alcohol formed are separated by distillation.

* * * * *